United States Patent [19]

Zysman et al.

[11] Patent Number: 5,773,611

[45] Date of Patent: Jun. 30, 1998

[54] CERAMIDES, PROCESS FOR THEIR PREPARATION AND THEIR APPLICATIONS IN THE COSMETIC AND DERMOPHARMACEUTICAL FIELDS

[75] Inventors: Alexandre Zysman, Paris; Guy Vanlerberghe, Claye-Souilly; Didier Semeria, Courtry, all of France

[73] Assignee: L'Oreal, Paris, France

[21] Appl. No.: 811,596

[22] Filed: Feb. 26, 1997

Related U.S. Application Data

[60] Continuation of Ser. No. 463,514, Jun. 5, 1995, abandoned, which is a division of Ser. No. 384,434, Feb. 2, 1995, Pat. No. 5,618,523, which is a continuation of Ser. No. 837,935, Feb. 20, 1992, abandoned.

[30] Foreign Application Priority Data

Feb. 21, 1991 [FR] France .................................. 91 02091

[51] Int. Cl.$^6$ .............................. A61K 7/00; A61K 7/48
[52] U.S. Cl. ......................... 424/401; 424/450; 514/579; 514/738; 514/846; 514/847
[58] Field of Search .................................. 424/401, 450; 514/579, 738, 846, 847

[56] References Cited

U.S. PATENT DOCUMENTS

| | | | |
|---|---|---|---|
| 3,821,372 | 6/1974 | Vanlerberghe et al. | 424/170 |
| 4,217,344 | 8/1980 | Vanlerberghe et al. | 424/60 |
| 4,666,711 | 5/1987 | Vanlerberghe et al. | 424/70 |
| 4,880,572 | 11/1989 | Fujita | 549/369 |
| 4,937,328 | 6/1990 | Schmidt | 536/18.6 |
| 5,110,987 | 5/1992 | Liotta | 564/303 |
| 5,124,081 | 6/1992 | Vanlerberghe | 424/450 |

FOREIGN PATENT DOCUMENTS

| | | |
|---|---|---|
| 0097059 | 12/1983 | European Pat. Off. . |
| 0278505 | 8/1988 | European Pat. Off. . |
| 86/260008 | 11/1986 | Japan . |
| 86/120308 | 6/1987 | Japan . |
| 85971A | 1/1987 | Luxembourg . |
| 1155712 | 6/1969 | United Kingdom . |
| 83/1571 | 5/1983 | WIPO . |

OTHER PUBLICATIONS

Journal of Organic Chemistry, vol. 46, No. 22, Oct. 23, 1981, pp. 4393–4398.
Chemistry and Physics of Lipids, vol. 13, Oct. 1974, pp. 109–116.
Chemical Abstracts, vol. 106, No. 12, Mar. 23, 1987, p. 348.
Chemical Abstracts, vol. 107, No. 20, Nov. 16, 1987, p. 479.
Weiss, B. et al, "Synthesis of Long Chain Fatty Acid Amines of Sphingosine and Dihydrosphingosine", J.A.C.S., vol. 80, 1958, pp. 4657–4658.
Downing, D. et al, "Skin Lipids: An Update", The Journal of Investigative Dermatology, vol. 88, No. 3, pp. 2s–6s (1987).
Torres, J. et al, "Mixed Anhydrides in Peptide Synthesis", Tetrahedron, vol. 43, No. 17, pp. 4031–4034 (1987).
Bodansky, "Synthesis of Peptides by Aminolysis of Nitrophenyl Esters", Nature, No. 4459, p. 685 (1955).
March, J., Advanced Organic Chemistry, Third Edition, John Wiley & Sons, New York, pp. 670–677 (1985).
Staab, H., "Syntheses Using Heterocyclic Amides (Azolides)", Angew, Chem. Internat. Edit. vol. 1, No. 7, pp. 357–367 (1962).
Shapiro, D., Chemistry of Sphingolipids, Hermann, Paris, Chapter 1 (1969).
Szoka, F. et al, "Procedure for Preparation of Liposomes with Large Internal Aqueous Space and High Capture by Reverse–Phase Evaporation", Proc. Natl. Acad. Sci. USA, vol. 75, No. 9, pp. 4194–4198 (1978).
Jordan, E., "Low Temperature Aminolysis of Methyl Stearate Catalyzed by Sodium Methoxide", J.A.O.C.S., vol. 38 (1961), pp. 601–605.
Lapidot, Y. et al, "Use of Esters of N–hydroxysuccinimide in the Synthesis of N–acylamino acids", Journal of Lipid Research, vol. 8 (1967), pp. 142–145.

*Primary Examiner*—Sally Gardner-Lane
*Attorney, Agent, or Firm*—Jacobson, Price, Holman & Stern, PLLC

[57] ABSTRACT

The invention relates to ceramides of formula:

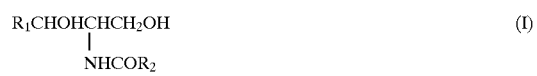

where $R_1$ denotes a $C_{11}$ to $C_{21}$ alkyl or alkenyl radical; $R_2$ denotes a $C_{11}$–$C_{19}$ hydrocarbon radical, which is linear and carries one or more ethylenic unsaturations, and in particular one or two, or a mixture of $C_{11}$–$C_{19}$ hydrocarbon radicals, which are linear, saturated or carry one or more ethylenic unsaturations, and in particular one or two, in which the proportion of saturated radicals cannot exceed 35%, these compounds being in the form of a racemic mixture of the erythro and threo diastereoisomers in the erythro:threo proportions of 85:15 to 60:40.

The invention also relates to the process for preparing the compounds as well as their applications in the cosmetic and dermopharmaceutical fields.

13 Claims, No Drawings

CERAMIDES, PROCESS FOR THEIR PREPARATION AND THEIR APPLICATIONS IN THE COSMETIC AND DERMOPHARMACEUTICAL FIELDS

This application is a continuation of application Ser. No. 08/463,514, filed Jun. 5, 1995, abandoned which is a division of application Ser. No. 08/384,434, now U.S. Pat. No. 5,618,523 filed Feb. 2, 1995, which is a continuation of application Ser. No. 07/837,935, filed Feb. 20, 1992, abandoned.

The subject of the present invention is novel ceramides, a process for their preparation as well as their use, in particular in the treatment and care of the skin and the hair in the cosmetic or dermopharmaceutical field.

Exposure of the skin to the cold, to the sun, to low relative humidity atmospheres, repeated treatments with washing compositions or alternatively contact with organic solvents, are factors which cause visible drying in various degrees. The skin appears drier, less supple and the skin relief more pronounced. Moreover, the hair, which is too often subjected to certain hair treatments, lose its shiny appearance and may become rough and fragile.

The applicant company has therefore sought out compounds which make it possible to prevent or correct these phenomena which translate into a visible drying and which restore to the skin its suppleness and to the hair its sheen and its softness.

To resolve this problem, the use of ceramides has already been proposed. It is indeed known that these compounds are the preponderant constituent elements of the intercorneocytic lipids of the stratum corneum and are involved in maintaining the integrity of the cutaneous barrier. They represent, according to DOWNING ("The Journal of Investigative Dermatology", vol. 88, No. 3, p. 2s.6s, 1987), about 40% of these lipids as a whole.

The ceramides used in the cosmetic field are natural extracts derived in particular from pork skin, cow brain, eggs, blood cells, plants and the like (Patent Applications JA 86/260008 and JA 87/120308). Such ceramides have also been proposed for hair protection (EP 0278 505).

Always involved therefore are mixtures with a more or less substantial ceramide content and whose composition is difficult to control. Furthermore, these mixtures are subject to bacterial contamination. Their preservation is very difficult to manage. When they are of animal orign, there is in addition a risk of contamination by the agent responsible for BSE (bovine spongi-form encephalopathy).

The applicant company therefore turned to synthetic ceramides in order to resolve these problems.

The applicant company has thus discovered novel compounds whose structure may be represented by the following formula;

$$R_1CHOHCHCH_2OH \atop | \atop NHCOR_2 \qquad (I)$$

in which:
R$_1$ denotes a C$_{11}$ to C$_{21}$ alkyl or alkenyl radical;
R$_2$ denotes a C$_{11}$–C$_{19}$ hydrocarbon radical, which is linear and carries one or more ethylenic unsaturations, and in particular one or two, or a mixture of C$_{11}$–C$_{19}$ hydrocarbon radicals, which are linear, saturated or carry one or more ethylenic unsaturations, and in particular one or two, in which the proportion of saturated radicals cannot exceed 35%, these compounds being in the form of a racemic mixture of the erythro and threo diastereoisomers in the erythro:threo proportions of 85;15 to 60:40.

The compounds (I) according to the invention which are low melting point waxes, therefore possess a very special advantage for the treatment and the care of the skin and the hair in the cosmetic or dermopharmaceutical field by making it possible to prevent or correct certain effects of the visible drying.

These compounds are moreover weakly aggressive towards the skin or the ocular mucous membranes and they are well tolerated by cellular membranes such as those of erythrocytes.

The above novel compounds of formula (I) possess emollient and demulcent properties. They are easily solubilised in the fatty phases of cosmetic or dermopharmaceutical preparations.

The hair strands treated with these compounds exhibit a shiny appearance and a lower sensitivity to water due to the supply of lipid material uniformly distributed on the scales of the hair strand. Their mechanical properties and vitality are also improved.

These compounds form vesicles in combination with other lipids.

The subject of the present invention is thus the novel ceramides of formula (I) defined above in the form of a racemic mixture of the erythro and threo diastereo-isomers in the proportions of 85:15 to 60:40.

The above ceramides of formula (I) result from the acylation of the amine functional group of a sphingosine or a dihydrosphingosine with an activated acid of formula R$_2$COA where R$_2$ has the meaning given above and A may in particular have the following meanings:

$$-Cl, -OCOC_2H_5, -O-\!\!\!\bigcirc\!\!\!-NO_2,$$

[cyclic imide structure], [phenyl-NH-C(=O)-N-cyclohexyl structure], $$-OCH_3, -OC_2H_5, -N\!\!\diagdown\!\!\diagup, -N\!\!\diagdown\!\!\diagup \text{ etc.} \ldots$$

In the present application, sphingosine or dihydrosphingosine will be understood to mean the D,L compounds, that is to say the racemic mixtures of the erythro and threo diastereoisomers.

Another subject of the present invention therefore consists in the process of preparation of the compounds of formula (I) which may be represented by the following scheme:

$$R_1CHOHCHCH_2OH \atop | \atop NH_2 \qquad \longrightarrow \qquad R_1CHOHCHCH_2OH \atop | \atop NHCR_2 \atop \| \atop O$$

(II)           (I)

R$_1$ and R$_2$ having the meanings given above.

The compounds (I) are obtained by acylation of the compounds of formula (II) either with an acid chloride or with an anhydride or with a para-nitrophenol ester or with a succinimide ester or with a dicyclohexyl-carbodiimide ester or with a lower alkyl ester or with an azolide, and in particular an imidazolide or a pyrazolide.

The acylation reactions with a lower alkyl ester take place in the anhydrous state. They are in particular described by E. F. JORDAN in JAOCS p. 600–605 (1961).

The other reactions are carried out in solvents such as tetrahydrofuran, pyridine, dimethylformamide, dichloromethane and the like.

The acylation with a succinimide and a dicyclohexylcarbodiimide ester is described in particular by LAPIDOT in J. Lipid Res. 8, 142–145 (1967).

The acylation with a para-nitrophenol ester is described in particular by BODANSKY in Nature No. 4459 p. 685 (1955).

The acylation with a mixed anhydride is described by J. L. TORRES in Tetrahedron vol. 43 No. 17, p. 4031–3 (1987).

The acylations with azolides are described by H. A. STAAB in Angew, Chem. Internat. Edit. Vol. 1 No. 7 p 357–367 (1962).

The acylation reactions are described in general by J. MARCH in Advanced Organic Chemistry-Third Edition—JOHN WILEY & SONS-INC p. 370–377 (1985).

The hydrochloride of the compound (II) may also be used for the preparation of the compound (I) of the invention.

The compounds (II) are known compounds. Their synthesis has been described in particular by D. SHAPIRO in "Chemistry of sphingolipids", HERMAN Paris (1969).

When $R_1$ denotes an alkenyl radical, the compounds (II) are sphingosines whose synthesis is described on page 21 of "Chemistry of Sphingolipids".

When $R_1$ denotes an alkyl radical, the compounds (II) are dihydrosphingosines. They may be prepared in particular from methyl or ethyl 2-acetamido-3-oxo-alkanoate as described in "Chemistry of Sphingo-lipids", page 32.

The methods of synthesis of sphingosines or dihydrosphingosines described above result in racemic mixtures of the erythro and threo diastereoisomers in the erytho-threo proportions of 85:15 to 60:40.

The compounds according to the invention may have various applications, in particular as waxy constituents in cosmetic or dermopharmaceutical compositions. These compounds possess, in addition, the property of forming vesicles in combination with other lipids when they are dispersed in water.

The subject of the present invention is therefore the use of lipid compounds of formula (I) as waxy constituents in emulsions, dispersions or in lotions. Its subject is also the use of these compounds, combined with other lipids, for the formation of lipid spherules.

The subject of the present invention is also compositions for cosmetic or dermopharmaceutical use containing a compound of formula (I).

Another subject of the invention consists of a process for the cosmetic treatment of the skin, the hair or hair strands consisting in applying to these a sufficient amount of such a composition containing a compound of formula (I).

The compositions according to the invention may be provided in the form of emulsions (milk or cream), dilute alcoholic, oily or oil-alcohol lotions, gels, dispersions or solid sticks, sprays or aerosol foams.

According to the invention, the compounds of formula (I) represent 0.05% to 20%, and preferably 0.1 to 10% of the total weight of the composition.

The compositions are for example emollient lotions, milks or creams, milks or creams for skin or hair care, make-up removing creams, lotions or milks, foundation bases, anti-sun lotions, milks or creams, artificial tanning lotions, milks or creams, shaving creams or foams, after-shave lotions, shampoos or mascaras.

These compositions may also be provided in the form of lipsticks intended either to colour the lips or to avoid chapping, or of eye makeup or face blushers and foundations.

While the compositions according to the invention are provided in the form of water-in-oil or oil-in-water type emulsions, the fatty phase is essentially composed of a mixture of the compound of formula (I) with at least one oil and, optionally, one other fatty substance.

The fatty phase of the emulsions may constitute 5 to 60% of the total weight of the emulsion.

The aqueous phase of the said emulsions preferably constitutes 30 to 85% of the total weight of the emulsion.

The proportion of the emulsifying agent may be between 1 and 20%, preferably between 2 and 12% of the total weight of the emulsion.

While the compositions according to the invention are provided in the form of oily, oil-alcohol or dilute alcoholic lotions, they may constitute, for example, anti-sun lotions containing a UV-ray absorbing screen, demulcent lotions for the skin; the oily lotions may in addition constitute foam oils containing an oil-soluble surface-active agent, bath oils and the like.

Among the main adjuvants which may be present in the compositions according to the invention, there may be mentioned fatty substances such as mineral, animal or vegetable oils or waxes, fatty acids, fatty acid esters such as fatty acid triglycerides having 6 to 18 carbon atoms, fatty alcohols; emulsifiers such as oxyethylenated fatty alcohols or polyglycerol alkyl ethers; solvents such as lower monoalcohols or polyalcohols containing 1 to 6 carbon atoms or alternatively water.

The mono- or polyalcohols most particularly preferred are chosen from ethanol, isopropanol, propylene glycol, glycerol and sorbitol.

By way of fatty substances, among the mineral oils, there may be mentioned liquid paraffin; among the animal oils, whale, seal, menhaden, halibut liver, cod, tuna fish, tortoise, neat's-foot, horse foot, sheep foot, vison, otter, marmot oils and the like; among vegetable oils, almond, wheat germ, olive, maize germ, jojoba, sesame, sunflower, palm, nut, karite, shorea, macadamia, blackcurrant seed oils and the like.

Among the fatty acid esters, there may be used esters of saturated or unsaturated $C_{12}$ to $C_{22}$ acids and lower alcohols such as isopropanol or glycerol, or linear or branched, saturated or unsaturated $C_8$ to $C_{12}$ fatty alcohols, or alternatively $C_{10}$–$C_{22}$ 1,2-alkanediols.

As fatty substances, petroleum jelly, paraffin, lanolin, hydrogenated lanolin, tallow, acetylated lanolin and silicone oils may also be mentioned.

Among the waxes, there may be mentioned Sipol wax, lanolin wax, beeswax, Candelilla wax, micro-crystalline wax, Carnauba wax, spermaceti, cacao butter, karite butter, silicone waxes, hydrogenated oils which are solid at 25° C., sucroglycerides, Ca, Mg and Al oleates, myristates, linoleates and stearates.

Among the fatty alcohols, there may be mentioned lauryl, cetyl, myristyl, stearyl, palmityl, oleyl and GUERBET alcohols such as 2-octyldodecanol, 2-decyltetra-decanol or 2-hexyldecanol.

As emulsifiers, among the polyoxyethylenated fatty alcohols, there may be mentioned the lauryl, cetyl, stearyl and oleyl alcohols containing 2 to 20 moles of ethylene oxide, and among the polyglycerol alkyl ethers, the $C_{12}$–$C_{18}$ alcohols containing 2 to 10 moles of glycerol, It may also be advantageous to use thickeners such as cellulose derivatives, polyacrylic acid derivatives, guar or carob gums or xanthan gum.

The composition according to the invention may also contain adjuvants generally used in the cosmetic or dermopharmaceutical field, and in particular moisturising products, demulcents, products for the treatment of skin disorders, sunscreen agents, germicides, colorants, preservatives, perfumes and propellants.

When the compositions according to the invention are dispersions, they may be dispersions of compounds of formula (I) in water in the presence of a surface-active agent or, alternatively, aqueous dispersions of lipid spherules composed of organised molecular layers enclosing an encapsulated aqueous phase, these layers being composed of at least one compound of formula (I) combined with at least one other lipid compound.

To that effect, there may be mentioned, as lipid compounds, long chain alcohols and diols, sterols such as cholesterol, phospholipids, cholesteryl sulphate and phosphate, long chain amines and quaternary ammonium derivatives thereof, dihydroxyalkylamines, polyoxyethylenated fatty amines, long chain amino alcohol esters, quaternary ammonium salts and derivatives thereof, fatty alcohol phosphoric esters such as dicetyl-phosphate acid or its sodium salt, alkyl sulphates such as sodium cetyl sulphate, fatty acids in the form of salts or, alternatively, lipids such as those described in French Patents No. 2,315, 991; 1,477,048 and 2,091,516 or in International Patent Application WO 83/01 571.

Lipids comprising a saturated or unsaturated, branched or linear, long lipophilic chain containing 12 to 30 carbon atoms, for example an oleyl, lanolin, tetradecyl, hexadecyl, isostearyl, lauryl or alkylphenyl chain may be used, for example, as other lipids. The hydrophilic group of these lipids may be an ionic or nonionic group. Groups derived from polyethylene glycol may be mentioned as nonionic groups. Polyglycerol ethers such as those described in French Patents No. 1,477,048; 2,091,516; 2,465,780 and 2,482,128 may also be used advantageously as lipids forming the lamellar phase.

A group derived from an amphoteric, anionic or cationic compound may be used advantageously as an ionic group.

Other lipids described in International Patent Application WO 83/01 571 as capable of being used for the formation of vesicles are glycolipids such as lactosyl-ceramide, galactocerebroside, gangliosides and trihexosylceramide as well as phospholipids such as phosphatidylglycerol and phosphatidylinositol.

The subject of the present invention therefore is also a dispersion of lipid spherules composed of organised molecular layers of compound(s) of formula (I) and of lipid defined above, enclosing an aqueous phase to be encapsulated.

The continuous phase of the dispersion which surrounds the spherules is an aqueous phase.

The sperules in dispersion have a diameter of between 0.05 μm and 5 μm.

The aqueous phase encapsulated in the spherules may be water or an aqueous solution of active substance and is in this case preferably isoosmotic with respect to the continuous phase of the dispersion.

The spherules may be obtained in particular using the process described in French Patent 2,315,991 by the applicant company, according to which a dispersion of spherules composed of organised molecular layers enclosing an aqueous phase to be encapsulated is prepared by bringing into contact, on the one hand, one or more lipid compounds of formula (I) combined with one or more lipid(s) defined above and, on the other hand, the aqueous phase to be encapsulated in the spherules, by stirring to ensure the mixing and to obtain a lamellar phase, by then adding a dispersion liquid in an amount greater than the amount of lamellar phase obtained, and by vigorously shaking for a period ranging from 15 minutes to 3 hours approximately.

The weight ratio between the aqueous phase to be encapsulated and the compound(s) of formula (I) combined with the lipids forming the lamellar phase is preferably between 0.1 and 20.

The weight ratio of the aqueous dispersion phase added to the lamellar phase that is dispersed is preferably between 2 and 100, the dispersion phase and the aqueous phase to be encapsulated being preferably iso-osmotic.

The stirring is performed by means of a shaker. The process is preferably implemented at a temperature of between 30° and 120° C.

Another preparation process may consist in using the process called REV (reverse-phase evaporation vesicle) described in Proc. Natl. Acad. Sci. USA., Vol. 75, No. 9, pages 4194–4198 (1978) by SZOKA and PAPAHADJOPOULOS.

The process may also be implemented which comprises the sequence of steps consisting in dissolving at least one lipid in at least one water-immiscible organic solvent; adding the organic phase thus obtained to an aqueous phase; forming a two-phase dispersion under vigorous stirring, it being possible for the size of the vesicles to be adjusted by varying the rate of stirring during this phase mixing; conducting the evaporation of the solvent(s) under vigorous stirring; and, where appropriate, concentrating the dispersion.

The active substances may be substances of interest in the pharmaceutical or food sector or substances having a cosmetic activity. When they are water-soluble, they are in the aqueous phase encapsulated inside the vesicles.

The water-soluble substances having a cosmetic and/or pharmaceutical activity may be products intended for the care or treatment of the skin and of the hair such as for example humectants such as glycerine, sorbitol, pentaerythritol, pyrrolidone carboxylic acid and its salts; artificial tanning agents such as dihydroxy-acetone, erythrulose, glyceraldehyde, γ-dialdehydes such as tartaric aldehyde, these compounds being optionally combined with colorants; water-soluble sunscreen agents; antiperspiration agents, deodorants, astringents, refreshing, tonic, cicatrisant, keratolytic or depilatory products, perfumed water; plant tissue extracts such as polysaccharides; water-soluble colorants; antidandruff agents; antiseborrhoeic agents, oxydants such as bleaching agents such as hydrogen peroxide; reducing agents such as thioglycolic acid and its salts.

Vitamins, hormones, enzymes such as superoxide dismutase, vaccines, anti-inflammatory agents such as hydrocortisone, antibiotics, bactericides, cytotoxic or anti-tumour agents may also be mentioned.

When the active substances are fat-soluble, they are incorporated into the vesicle layers. There may be chosen from the group consisting of fat-soluble sunscreen agents, substances intended to improve the condition of dry or aged skin, tocopherols, vitamins E, F or A and esters thereof, retinoic acid, antioxidants, essential fatty acids, glycyrrhetinic acid, keratolytic agents and carotenoides.

A water-immiscible liquid phase L may also be added to the aqueous phase of the dispersions of spherules according to the invention. In particular, the composition according to the invention may contain 2 to 70% by weight of water-immiscible liquid phase L relative to the total weight of the composition, the relative proportion by weight of the constituent lipid(s) of the vesicles relative to the dispersed liquid phase L being between 0.02/1 and 10/1.

The constituent(s) of the dispersed liquid phase L in the aqueous phase D may be chosen from the group consisting of oils such as esters of fatty acids and polyols, and esters of fatty acids and branched alcohols of formula $R^7$—$COOR^8$, formula in which $R^7$ represents a higher fatty acid residue containing 7 to 19 carbon atoms and $R^8$ represents a branched hydrocarbon chain containing 3 to 20 carbon atoms; hydrocarbons such as hexadecane, paraffin oil, perhydrosqualene; halogenated hydrocarbons such as perfluorodecahydro-naphthalene; perfluorotributylamine; polysiloxanes; organic acid esters, ethers and polyethers. The liquid phase L may enclose at least one perfume and/or at least one fat-soluble active substance. Such fat-soluble substances may be composed of fat-soluble sunscreen agents, substances intended to improve the condition of dry or aged skin, tocopherols, vitamins E or F, vitamin A and esters thereof, retinoic acid, antioxidants, essential fatty acids, glycyrrhetinic acid, keratolytic agents and carotenoides.

Various adjuvants such as opacifiers, gelling agents, fragrances, perfumes or colorants may also be added to the dispersions of spherules according to the invention.

The dispersions of lipid spherules according to the invention possess the advantage of carrying active substances which are thus masked and protected with respect to various modifying agents: oxidants and more generally compounds which are reactive with respect to encapsulated active substances. The penetration and the binding of active substances may be modulated by varying the size of the spherules and their electrical charge. The action of these active substances may thus be also deferred (delayed action). Finally, it is possible, by virtue of the use of lipids (I) according to the invention and of combined active substances, to obtain a specific beneficial, and at the same time suppling, action of the active substance used which is particularly advantageous in the case of skin treatment.

The subject of the present invention therefore is also the use in cosmetics of an aqueous dispersion of spherules composed of organised molecular layers of lipid compounds (I) combined with other lipids enclosing an aqueous phase to be encapsulated, in particular for skin treatment.

The subject of the invention is also the use of such a dispersion of lipid spherules in the dermopharmaceutical field or in the food industry.

The present invention will be more clearly illustrated by the following non restrictive examples.

EXAMPLE 1
Preparation of 2-oleoylamino-1,3-octadecanediol
1st stage
Preparation of the compound (II) with: $R_1=C_{15}H_{31}$ :
2-Amino-1,3-octadecanediol hydrochloride (erthyro/threo mixture)

Methyl 2-acetamido-3-oxooctadecanoate (100 g, that is 0.27M) is suspended in 1 liter of absolute ethanol. The temperature of the reaction mixture is brought below 0° C. At this temperature, 30.7 g (0.8M) of sodium borohydride are added in three portions and the stirring is maintained at this temperature for 3 hours. The reaction mixture is then heated at a reflux temperature of the solvent for 3 hours. After cooling to room temperature, 140 cm$^3$ of concentrated hydrochloric acid are added and the reaction mixture is again refluxed for 3 hours. This mixture is filtered while it is still hot on a sintered glass. The filtrate is concentrated to dryness under reduced pressure.

The solid obtained is recrystallised in 300 cm$^3$ of a heptane:ethyl acetate=90:10 solvent mixture. 88 g of a white solid are isolated whose acid value, measured in ethanol using a N/10 solution of sodium hydroxide, is 2.99 meq/g.

The $^{13}$C NMR spectrum of this solid is in conformity with the expected structure.

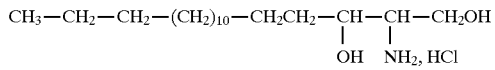

It is indeed dihydrosphingosine hydrochloride in the form of a D,L erythro-threo racemic mixture.

2nd stage

Preparation of the compound (I) in which —$COR_2$=oleoyl

Raw materials

| | |
|---|---|
| dihydrosphingosine hydrochloride prepared in the first stage | 100 g |
| oleoyl chloride (1) | 84.7 g |
| triethylamine | 60 g |
| tetrahydrofuran | 400 ml |
| isopropanol | 150 ml |
| AMBERLITE IRN 150 resin | 160 g |
| ethyl acetate | 600 ml |

(1) Marketed by BASF with an acid chloride titre of 98%.

(1) Marketed by BASF with an acid chloride titre of 98%. The distribution of the principal chains is as follows:

| | |
|---|---|
| $C_{14}$: 4.5% | $C_{18}$ = 1: 65% |
| $C_{16}$: 8.5% | $C_{18}$ = 2: 4.8% |
| $C_{18}$: 3.4% | $C_{18}$ = 3: 0.5% |

Procedure 400 ml of tetrahydrofuran and 100 g of dihydrosphingosine hydrochloride (0.296 mol) are introduced into a reactor under nitrogen and dispersed by heating to 45° C.; 31 g of triethylamine (0.307 mol) are then added, causing cloudiness of the rection mixture and a rise in temperature to 48° C.; the "apparent" pH is now 8.3±0.1. The mixture is allowed to reequilibrate to 30° C.±1° C.

Using a dropping funnel, the addition of oleoyl chloride is then started until the "apparent" pH is brought to 6.7 and it is maintained at this value by adding simultaneously, over 1 hour, the remainder of the oleoyl chloride and 29 g of triethylamine (0.287 mol); during these additions, the temperature rises to 33° C. and is maintained at this value. The reaction is then continued for an additional two and a half hours.

At the end of the reaction, the reaction mixture is washed three times with 200 ml of water at 50°–60° C., freed from tetrahydrofuran by distillation under reduced pressure, and taken up in 200 ml of isopropanol at 50° C. The cloudy solution obtained is stirred for one hour in the presence of 180 g of AMBERLITE IRN 150 resin and then filtered on a preheated No. 4 sintered glass; after washing the resin with 50 ml of isopropanol at 60° C., the clear yellow solution is slowly poured into 600 ml of ethyl acetate under vigorous stirring. The precipitate obtained is allowed to stand for 15 hours at ±4° C. and then drained on a No. 3 sintered glass. After drying under reduced pressure at 40°–45° C., 64 g of white product are obtained, that is a yield of 40%.

| ANALYSES |  |  |  |
|---|---|---|---|
| m.p. = 76° C. |  |  |  |
| IR spectrum conforms |  |  |  |
| $1_H$ NMR spectrum conforms |  |  |  |
| elemental analysis: |  |  |  |

| | C % | H % | N % | O % |
|---|---|---|---|---|
| Calculated | 76.40 | 12.65 | 2.48 | 8.48 |
| Found | 76.55 | 12.65 | 2.49 | 8.63 |

Erythro:threo ratio = 75:25

EXAMPLE 2
Preparation of 2-oleoylamino-1,3-octadecanediol 3 ml of ethyl chloroformate (31 mmol) in 5 ml of tetrahydrofuran are solubilised in a round-bottomed flask under an inert atmosphere; this solution being cooled to −15° C., 11.3 g of triethylamine oleate (29.5 mmol) previously solubilised in 10 ml of tetrahydrofuran, are added dropwise.

After stirring for 2 hours at room temperature, the reaction mixture is slowly poured, under an inert atmosphere, into 8.9 g of (D,L)-2-amino-1,3-octadecane-diol prepared in the 1st stage of Example 1 (29.5 mmol) solubilised in 40 ml of tetrahydrofuran at 30° C.

After stirring for 1 hour at 30° C., under an inert atmosphere, (thin layer chromatography on silica gel, eluent methylene chloride/methanol/ammonium hydroxide 15/3.5/0.6), the reaction mixture is washed with water and then evaporated to dryness under vacuum. The crude product obtained is chromatographed on a silica column (eluent: ethyl acetate/heptane 5/3) and 12.5 g of white crystals (yield 75%) are obtained after evaporation of the elution solvent under vacuum.

The $^3C$ NMR and IR spectra are in conformity with the expected structure.

| Percentage analysis: $C_{36}H_{71}NO_3$ |  |  |  |
|---|---|---|---|
| | C % | H % | N % | O % |
| Calculated | 76.40 | 12.65 | 2.48 | 8.48 |
| Found | 76.47 | 12.75 | 2.60 | 8.72 |

Erythro:threo ratio = 84:16

EXAMPLE 3
Preparation of 2-linoleoylamino-1,3-octadecanediol 11.6 g of white crystals (yield 70%) are obtained using the same procedure as that described in Example 2 and using 11.3 g of triethylamine linoleate (29.5 mmol).

The $^{13}C$ NMR and IR spectra are in conformity with the expected structure

| Percentage analysis: $C_{36}H_{68}NO_3$ |  |  |  |
|---|---|---|---|
| | C % | H % | N % | O % |
| Calculated | 76.67 | 12.33 | 2.48 | 8.51 |
| Found | 76.74 | 12.38 | 2.49 | 8.64 |

Erythro:threo ratio = 74:26

EXAMPLE 4
Preparation of 2-linoleoylamino-1,3-octadecandiol 11.6 g of white crystals (yield 49%) are obtained using the same procedure as that described in Example 2 and using 11.3 g of triethylamine linoleate *(29.5 mmol).

*From a commercial vitamin F whose composition is as follows:

The $^{13}C$ NMR spectrum is in conformity with the expected structure.

The mass spectrum is in accordance with the expected structure.

Erythro:threo ratio=66:34

| $C_{14}$: | 0.1% |
|---|---|
| $C_{16}$: | 6.5% |
| $C_{18} = 1$: | 15.5% |
| $C_{18} = 2$: | 72.4% |
| $C_{18} = 3$: | 3.4% |

FORMULATION EXAMPLES

Example 1
Vesicular dispersion

The preparation is produced using the following parts:

Part A ceramide according to Example 1: 0.90 g sodium cholesterol sulphate: 0.60 g Part B water:1.50 g Part C:

0.1M phosphate buffers, pH 6.93: 27.10 g

Stage 1

The constituents of part A are introduced into a 100-ml round-bottomed flask and then dissolved in a mixture containing 5 ml of chloroform and 20 ml of methanol. The solvent is then evaporated at 40° C. under reduced pressure (final pressure: about $5 \times 10^2$ Pa) using a rotary evaporator.

Stage 2

The lipid film formed at the end of stage 1 is removed and placed in a 15-ml bottle. Part B is added to the lipids. The mixture obtained is subjected to the following cycle; homogenisation using a spatula—heating in an oven at 75° C. for a period of 15 minutes; reequilibration to room temperature by spontaneous cooling in the open. The cycle is repeated by heating once for 15 minutes and then heating again for 5 minutes.

Stage 3

Part C is added to the lamellar phase derived from stage 2. The mixture thus obtained is stirred by shaking for 1 hour at 70° C.

A white dispersion of vesicles is thus obtained. The volume fraction of the vesicles is equal to 18% and their encapsulation level is equal to 2.6 μl of aqueous medium per mg of lipid mixture.

Example 2
Vesicular dispersion

The preparation is produced using the following parts:

Part A nonionic compound I: 0.56 g

I: general formula: $C_{16}H_{33}O-[-C_3H_5-(OH)-O-]_n-H$ where: $-C_3H_5$ (CH)—O is represented by the following structures taken in a mixture or separately:

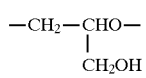

-continued

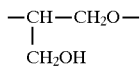

where n has a mean statistical value equal to 3 cholesterol: 0.71 g sodium dihexadecyl phosphate: 0.08 g ceramide according to Example 1: 0.15 g Part B solution containing 0.02% of sodium nitride in water: 28.50 g Stage 1

The constituents in part A are introduced into a 100-ml round-bottomed flask and then dissolved in a mixture containing 10 ml of dichloromethane and 4 ml of methanol.

The solvent is then evaporated at 41° C. under reduced pressure, stepwise from atmospheric pressure down to about $5 \times 10^2$ Pa, using a rotary evaporator.

Stage 2

Part B is added to the lipid film formed at the end of stage 1. The mixture thus obtained is stirred by shaking for 2 hours at 70° C.

A white dispersion of vesicles is thus obtained.

The volume fraction of the vesicles is equal to 53% and their encapsulation level is equal to 9.4 μl of aqueous mixture per mg of lipid mixture.

Stage 3

The dispersion obtained at the end of stage 2 is heated to a temperature of 30° C. and treated for 2 minutes using an ultrasound homogeniser (Sonifier B 3.0 sold by BRANSON SONIC POWER Co), equipped with a microprobe.

Adjusting conditions:

working cycle: 50% power adjustment: position 5

A whitish dispersion of vesicles is thus obtained.

The volune fraction of the vesicles is equal to 19% and their encapsulation level is equal to 2.9 μl of aqueous mixture per mg of lipid mixture.

The mean size of the vesicles measured after storing at room temperature for 1 day is equal to (182±4) nm; for one week: (179±3) nm; for 1 month; (177±4) nm.

Example 3

| Skin care: O/W cream | (% by weight) |
|---|---|
| glycerol stearate | 2 |
| sorbitan monostearate containing 20 moles of ethylene oxide | 1 |
| cetyl alcohol | 0.5 |
| stearic acid | 1.4 |
| triethanolamine | 0.7 |
| crosslinked polyacrylic acid marketed under the name "CARBOPOL 940" | 0.4 |
| liquid fraction of karite fat | 12 |
| synthetic perhydrosqualene | 12 |
| antioxidants | 0.05 |
| ceramide in accordance with Example 1 or 2 | 0.2 |
| perfume | 0.5 |
| water + preservatives qs | 100 |

Example 4

| Skin care: O/W cream | (% by weight) |
|---|---|
| sorbitan monoisostearate | 5 |
| microcrystalline wax | 1 |
| liquid paraffin | 10 |
| maize germ oil | 4 |
| esters of $C_8$–$C_{18}$ fatty acids and $C_{12}$–$C_{18}$ fatty alcohols | 1 |
| octyldodecanol | 4.9 |
| ceramide in accordance with Example 1 or 2 | 0.35 |
| modified montmorillonite and neutral oil gel (caprylic and capric acid triglycerides) | 5 |
| propylene glycol | 3 |
| antioxidants | 0.1 |
| water + preservatives qs | 100 |

Example 5

| Skin care: body milk | (% by weight) |
|---|---|
| glycerol stearate | 2 |
| sorbitan monostearate containing 20 moles of ethylene oxide | 1 |
| stearic acid | 1.4 |
| triethanolamine | 0.7 |
| crosslinked polyacrylic acid marketed under the name "CARBOPOL 940" | 0.2 |
| sweet-almond oil | 3 |
| liquid paraffin | 8 |
| antioxidants | 0.05 |
| ceramide in accordance with Example 1 or 2 | 0.3 |
| water + preservatives qs | 100 |

Example 6

| Lipstick | (% by weight) |
|---|---|
| sesame oil | 25 |
| lanolin | 20 |
| Carnauba wax | 20 |
| ceramide in accordance with Example 1 or 2 | 5 |
| pigments | 10 |
| liquid paraffin | 100 |

Example 7

| Lipstick | (% by weight) |
|---|---|
| jojoba oil | 20 |
| lanolin | 25 |
| microcrystalline wax | 20 |
| ceramide in accordance with Example 1 or 2 | 5 |
| pigments | 10 |
| capric/caprylic acid triglycerides sold under the name "MIGLYOL 812" qs | 100 |

Example 8

| Vesicular dispersion | |
|---|---|
| The following products: | |
| ceramide from Example 1 | 120 mg |
| cholesterol | 75 mg |

-continued

| Vesicular dispersion | |
|---|---|
| palmitic acid | 75 mg |
| sodium cholesteryl sulphate | 30 mg | are dissolved in 10 ml of a solvent mixture (chloroform-methanol in a 2/1 ratio), in a 100-ml round-bottomed flask.

The solvent is evaporated using a rotary evaporator and the last traces of solvent are removed by passing through a vane pump for 1 hour.

The combination of lipids obtained is brought in contact with 10 g of deionised water in which 17.7 mg of potassium dihydrogen phosphate and 75.5 mg of disodium monohydrogen phosphate have been dissolved.

The mixture is homogenised using a shaker for 2 hours at a temperature of 90° C. and then is allowed to reequilibrate progressively to room temperature.

A dispersion of lipid vesicles whose mean size is 0.2 micron is thus obtained.

Example 9

Shampoo

A clear shampoo with the following composition is prepared:

| | |
|---|---|
| ceramide from Example 1 | 0.5 g |
| sodium chloride | 5 g |
| triethanolamine lauryl sulphate containing 40% AS (active substance) | 20 g AS |
| triethanolamine qs | pH 7 |
| water qs | 100 g |

Example 10

Hair lotion

A nonrinsing lotion with the following composition is prepared:

| | |
|---|---|
| ceramide from Example 1 | 0.4 g |
| decamethylcyclopentasiloxane sold under the name "SILBIONE 70045 V 5" by RHONE POULENC | 20 g |
| octamethylcyclotetrasiloxane sold under the name "SILBIONE 70045 V 2" by RHONE POULENC | 20 g |
| hexamethyldisiloxane sold under the name "HUILE AK 0.65" by WACKER | 19.6 g |
| ethyl alcohol | 100 g |

Example 11

Hair care

A nonrinsing care for damaged hair of the following composition is prepared:

| | |
|---|---|
| decamethylcyclopentasiloxane | 12.5 g |
| octamethylcyclotetrasiloxane | 12.5 g |
| ceramide from Example 1 | 0.1 g |
| mixture of a polydimethylsiloxane (13%) with a hydroxylated chain end and cyclomethicone (87%) sold under the name "Q2- 1401" by DOW CORNING | 65 g |
| $C_{12}$–$C_{15}$ fatty alcohol benzoate sold udner the name "FINSOLV TN" | 4.95 g |
| ethyl alcohol | 100 g |

This composition facilitates hair-styling, imparts sheen and form retention to the hair style.

Example 12

| Restructuring foam | |
|---|---|
| ceramide from Example 1 | 1 g |
| oxyethylated sorbitan monolaurate containing 20 moles of ethylene oxide sold under the name "TWEEN 20" by ICI | 5 g |
| preservatives | |
| water qs | 100 g |
| pH = 5.8 | |
| Packaging in aerosol cans | |
| active component | 92 g |
| hydrocarbon propellant sold under the commercial name "AEROGAZ 3.2N by ELF Aquitane | 8 g |

Applied without rinsing to bleached hair after shampooing, the composition improves the disentangling of wet hair and imparts a smooth and uniform feel.

Example 13

| After-shampoo | |
|---|---|
| mixture of cetyl stearyl alcohol and oxyethylenated cetyl stearyl alcohol and containing 33 moles of ethylene oxide sold under the name "SINNOWAX AO" by HENKEL | 2 g |
| cetyl alcohol | 1 g |
| stearyl alcohol | 1 g |
| hydroxyethyl cellulose sold under the name "NATROSOL 250 HR" by HERCULES | 1 g |
| ceramide from Example 1 | 0.5 g |
| preservatives | |
| water qs | 100 g |
| pH = 6 | |

Applied to bleached hair after shampooing, the composition imparts a feeling of greater firmness and greater uniformity to the hair.

Example 14

| Mascara | |
|---|---|
| triethanolamine stearate | 15 g |
| paraffin | 5 g |
| beeswax | 4 g |
| Carnauba wax | 4 g |
| ceramide from Example 1 | 0.5 g |
| gum arabic | 0.8 g |
| black iron oxide | 5 g |
| propyl para-hydroxybenzoate | 0.08 g |
| methyl para-hydroxybenzoate | 0.24 g |
| water qs | 100 g |

PROCEDURE

1—The waxes are melted (80° C.) and the pigment is incorporated therein.

2—The aqueous phase containing the gum and the preservatives is heated.

3—The two phases are adjusted to 75° C. and the ceramide is added to the waxy phase.

4—These two phases are mixed in order to produce the emulsion.

We claim:

1. Composition for cosmetic or dermopharmaceutical use, comprising, in the presence of an adjuvant selected from the group consisting of mineral, animal and vegetable oils and waxes, fatty acids, fatty acid esters, fatty alcohols, solvents, water, thickeners, emulsifiers, moisturizing products, demulcents, sunscreen agents, germicides, colorants, preservatives, perfumes, propellants and surface-active agents, 0.05 to 20% by weight of 2-oleoyl-1,3-octadecanediol (erythro/threo; D,L)

in the form of a racemic mixture of the erythro and threo diastereoisomers in the erythro:threo proportions of 85:15 to 60:40.

2. Composition according to claim 1 comprising 0.1 to 10% by weight of 2-oleoyl-1,3-octadecanediol.

3. Composition according to claim 1, in the form of an emulsion whose fatty phase, representing 5 to 60% of the total weight of the emulsion, consists essentially of a mixture of 2-oleoyl-1,3-octadecanediol with at least one oil, the aqueous phase constituting 30 to 85% of the total weight of the emulsion, the emulsifying agent being present in an amount of 1 to 20% by weight relative to the total weight of the emulsion.

4. Composition according to claim 3, wherein the emulsifying agent is present in an amount of 2 to 12% by weight relative to the total weight of the emulsion.

5. Composition according to claim 1, in the form of an oily, oil-alcohol or water-alcohol lotion, in the form of a gel, a dispersion, solid sticks, a spray or an aerosol foam.

6. Composition according to claim 1, in the form of an aqueous dispersion of lipid spherules composed of organized molecular layers enclosing an encapsulated aqueous phase, these layers being composed of 2-oleoyl-1,3-octadecanediol and at least one other lipid compound.

7. Composition in the form of an aqueous dispersion of lipid spherules according to claim 6, wherein the spherules have a diameter of between 0.05 μm and 5 μm.

8. Composition in the form of an aqueous dispersion of lipid spherules according to claim 6, wherein the aqueous phase encapsulated in the spherules is water or an aqueous solution of active substance.

9. Composition in the form of an aqueous dispersion of lipid spherules according to claim 6, wherein the aqueous phase encapsulated in the spherules is water or an aqueous solution of a substance having pharmaceutical or cosmetic activity.

10. Composition in the form of an aqueous dispersion of lipid spherules according to claim 6, wherein the aqueous phase encapsulated in the spherules contains at least one cosmetic and/or pharmaceutical, water-soluble active substance selected from the group consisting of humectants, artificial tanning agents optionally combined with colorants, water-soluble sunscreen agents, antiperspiration agents, deodorants, astringents, tonic products, cicatrising products, keratolytic agents, depilatory products, perfumed water, plant tissue extracts, water-soluble colorants, antidandruff agents, antiseborrhoeic agents, oxidants, reducing agents, vitamins, hormones, enzymes, vaccines, anti-inflammatory agents, antibiotics, bactericides and cytotoxic and antitumor agents.

11. Composition in the form of an aqueous dispersion of lipid spherules according to claim 6 containing at least one fat-soluble active substance selected from the group consisting of fat-soluble sunscreen agents, substances intended to improve the condition of dry and aged skin, tocopherols, vitamins E, F and A and esters thereof, retinoic acid, antioxidants, essential fatty acids, glycyrrhetinic acid, keratolytic agents and carotenoides.

12. Composition in the form of an aqueous dispersion of lipid spherules according to claim 6, further comprising 2 to 70% by weight of a water-immiscible liquid phase selected from the group consisting of oils, hydrocarbons, halogenated hydrocarbons, perfluorotributylamine, polysiloxanes, organic acid esters, ethers and polyethers.

13. Process for the cosmetic treatment of the skin, the hair or hair strands, consisting in applying to the skin, the hair or the hair strands a cosmetically effective amount of a composition according to claim 1.

* * * * *